United States Patent [19]

Marsoner et al.

[11] Patent Number: 5,039,490
[45] Date of Patent: Aug. 13, 1991

[54] SENSOR ELEMENT FOR DETERMINATION OF CONCENTRATION OF SUBSTANCES

[75] Inventors: Hermann Marsoner, Steinberg; Herbert Kroneis, Graz; Hellfried Karpf, Graz; Otto S. Wolfbeis, Graz; Helmut List, Graz; Alfred Leitner, Graz, all of Austria

[73] Assignee: AVL AG, Schaffhausen, Switzerland

[21] Appl. No.: 40,163

[22] Filed: Apr. 17, 1987

[30] Foreign Application Priority Data

Apr. 23, 1986 [AT] Austria ............................... 1094/86
Oct. 10, 1986 [AT] Austria ............................... 2707/86

[51] Int. Cl.$^5$ ........................................... G01N 31/00
[52] U.S. Cl. .............................. 422/82.01; 422/82.09; 422/88; 422/90; 422/91; 356/402; 356/416; 356/445; 356/446; 250/216; 250/574
[58] Field of Search ............... 436/172, 164, 805, 806; 422/55, 57, 82.01, 82.09, 88, 90, 91; 356/435, 219, 222, 402, 416, 445, 446; 250/216, 574

[56] References Cited

U.S. PATENT DOCUMENTS

| 3,625,756 | 12/1971 | Taguchi | 422/95 |
|---|---|---|---|
| 3,676,820 | 7/1972 | Taguchi | 422/95 |
| 4,324,760 | 4/1982 | Harris | 422/95 |
| 4,324,761 | 4/1982 | Harris | 422/95 |
| 4,568,518 | 2/1986 | Wolfbeis et al. | |

FOREIGN PATENT DOCUMENTS

| 105870 | 10/1983 | European Pat. Off. . |
| 109958 | 10/1983 | European Pat. Off. . |
| 109959 | 10/1983 | European Pat. Off. . |
| 106086 | 5/1974 | Fed. Rep. of Germany . |
| 2508637 | 11/1979 | Fed. Rep. of Germany . |

Primary Examiner—David A. Simmons
Assistant Examiner—Thi Dang
Attorney, Agent, or Firm—Watson, Cole, Grindle & Watson

[57] ABSTRACT

Due to the size of the devices used for the excitation and measuring of light, conventional sensor elements for optically determining the concentrations of substances contained in gaseous and liquid samples, featuring an indicator layer with one or more indicator substances, are not well suited for use with microanalysis equipment, nor are they easy to mass-produce. These disadvantages are eliminated by using a unitary sensor element having a carrier layer, at least one photosensitive element with electric contact leads in contact with the carrier layer, and an indicator layer containing an indicator substance.

18 Claims, 3 Drawing Sheets

SENSOR ELEMENT FOR DETERMINATION OF CONCENTRATION OF SUBSTANCES

BACKGROUND OF THE INVENTION

This invention relates to a sensor element for determining the concentrations of substances contained in gaseous or liquid samples, comprising a carrier layer and an indicator layer with one or more indicator substances whose optical properties, or at least one of them, will change upon interaction with the substance to be measured, depending on the latter's concentration.

DESCRIPTION OF THE PRIOR ART

Optical sensors for determining the concentrations of substances by means of indicators, in particular sensors based on a change in the fluorescent properties of the indicator upon interaction with the substance to be measured, have been state of the art for a considerable time. For example, DE-PS 25 08 637 presents a sensor element of the above type, in which a thin layer of the indicator solution is deposited on a suitable carrier material, the indicator solution being covered by a membrane which is permeable to the substance to be measured. On the carrier side of this configuration a complex lighting and photometric assembly is located, comprising a number of optical elements, both in the path of the excitation radiation and in that of the fluorescent radiation.

In an arrangement described in DD-PS 106 086 the fluorescent indicator is contained in a layer extending over a measuring chamber and a reference measuring chamber; in this instance, however, the indicator layer is shielded against the medium to be measured in the area of the reference measuring chamber. From the difference in fluorescence intensities obtained in the measuring chamber and in the reference measuring chamber, the concentration of the substance to be measured is directly inferred. The fluorescent light from the two measuring chambers is fed into a photoelectric converter by means of respective optical fiberguides.

The above sensors thus usually consist of a reaction space which may be configured as a thin layer and which contains the indicator substance in a given geometrical arrangement. From a position facing away from the sample, light of a given wavelength is transmitted to the indicator layer by means of a light source and suitable optical devices, such as lightguides or optical fibers. The fluorescent light, which is diffusely reflected and emitted in all directions by the indicator layer, is carried to a photodetector from the same side of the reaction space or the indicator layer, again with the use of suitable optical devices and filters. The side of the reaction space facing away from the optical devices is brought into contact with the gaseous or liquid sample, the substance to be measured usually entering the reaction space by diffusion and interacting with the indicator molecules of the indicator substance, whose optical properties, above all absorption and fluorescent properties, will change thereupon, depending on the concentration of the substance. There is a functional relationship between the degree and character of the change and the particle concentration to be measured.

The size of such configurations is determined by the size of the sensor itself on the one hand, and by the geometry and size of the optical devices required for picking up the fluorescent and/or reflected radiation on the other hand.

SUMMARY OF THE INVENTION

It is an object of the present invention to miniaturize such sensors which are used in microanalysis equipment, for instance, and to make them easy to mass-produce while providing as many reaction spaces or indicator layers of a known kind as possible.

In the present invention this object is achieved by integrating on the carrier layer one or more photosensitive elements including their electric contacts in planar arrangement and by establishing optical contact between the indicator substance of the indicator layer excited by the excitation radiation, and the photosensitive element(s). All layers of the electro-optical sensor are produced by standard microelectronic or photolithographic techniques, such as evaporation coating, sputtering, spinning, etching, ion beam erosion, etc., the required extreme miniaturization of the entire sensor unit, including the devices for picking up the fluorescent and/or reflected radiation, being achieved by the integration of the photosensitive elements and their electric contacts in a thin-film substrate of the sensor element, for instance. In this way the radiation to be measured is already picked up in the sensor element, which will eliminate the need for any photometric devices outside the sensor element. The measuring signals are directly transmitted to an electronic display/ evaluation unit via electric leads.

Integrating the electric contacts of the opto-electric elements into the sensor element does not represent any restriction in terms of the invention as the respective contact paths can also be established by known microelectronic techniques.

Preferably, a sensor element as specified by the invention is provided with known indicator layers that are optimized for specific tasks. Various types of indicator layers for such optical sensors, which are based on changes in absorption or fluorescence of indicator molecules, in particular for measuring oxygen, $CO_2$ and pH-values or other ionic concentrations, are known from European Pat. No. 0 109 958, European Pat. No. 0 109 959 (see corresponding U.S. Pat. No. 4,657,736) and European Patent No. 0 105 870, and are well suited for use in the context of the present invention.

It is also possible, of course, to use a sensor layer in accordance with U.S. Pat. No. 4, 568,518, in which a carrier membrane, e.g., made of cellulose, is penetrated by an independent network built from a material containing an indicator and reactive groups.

In order to create better conditions of excitation for the indicator substance, or to improve conditions for separating the excitation radiation from the radiation to be measured, an enhanced variant of the invention specifies in case of a given geometry that between a substrate containing the photosensitive elements and featuring at least one zone transparent to the excitation radiation and the indicator layer a coupling layer is provided which is transparent to the excitation radiation and the radiation to be measured. The optically transparent coupling layer, for instance an $SiO_2$ layer, can be applied by a suitable microelectronic technique, such as sputtering. The thickness of this layer will depend on the geometry of the topographical arrangement of the individual photosensitive elements. The substrate with the photosensitive elements also may consist of the same material as the coupling layer, if the photosensitive elements and their electric contacts are directly applied on the carrier layer and are then embedded into the coupling layer. On top of the individual elements or the optical coupling layer an indicator layer is placed, which is usually made from a polymer material and contains the fluorescent indicator, and which covers the entire element.

For better optical geometric separation of the excitation radiation and the radiation to be measured, it is proposed in a further development of the invention that the coupling layer with a refractive index $n_2$, together with the boundary layers on both sides with a refractive index $n_1$, should constitute a planar lightguide for the radiation to be measured, with $n_2 > n_1$, and that the boundary layer adjacent to the sample should have at least one recess which is covered by the indicator layer, and that each recess—seen in the direction of the excitation radiation—should be situated above a zone transparent to the excitation radiation, and, further, that there should be no total reflection of the radiation to be measured in the area of the photosensitive elements. The layers of glass required for the lightguide may be applied by reaction-supported sputtering. The light-guiding center layer or coupling layer should be thicker than 1 $\mu$m, i.e., it should amount to a multiple of the wavelength of the radiation to be measured, in order to be a good lightguide. The boundary layers on both sides of the center layer should be 1–2 $\mu$m thick to have a dimension sufficient for the evanescent field of the wave to be guided. In this configuration divergence of the excitation radiation is of little import as the outermost rays will be lost due to the steep angle at the boundary layer $n_2/n_1$.

An especially favorable variant of the invention provides that there should be only one zone transparent to the excitation radiation, and that the photosensitive element, for example a photodiode, should have an annular structure concentric thereto. Such a sensor may be obtained by etching an annular diode structure out of a wafer that already includes all the layers of a photodiode. By means of a sputtering technique the circular center opening obtained in this way is then filled up homogeneously with glass with a refractive index $n_1$. On top of this another layer of glass or plastic with a refractive index $n_2$ is deposited by sputtering or spinning. $n_2$ must be greater than $n_1$ in order to achieve total reflection in the layer with the refractive index $n_2$. From the topmost layer a central disk is etched out to make room for the sensor layer. Subsequent to this a hole is bored into the original substrate as far down as to the first layer of glass, in order to provide access for the excitation radiation. Into the central recess for the sensor layer the pigment silicone layer (refractive index $n_2$) is deposited, in order to obtain a gas sensor, for example. It is essential that the silicone layer should have a refractive index similar to that of the layer underneath, such that the entire sensor volume can be fully utilized.

A special variant of the invention provides that transparent zones be positioned in the substrate at an angle, i.e., the excitation radiation should strike the indicator layer at an angle $\alpha$ of 40°–60° preferably, exciting the areas of the indicator layer situated on top of the photosensitive elements. If this configuration is used, excitation of the areas of the indicator layer situated on top of the photosensitive elements will be particularly effective and the signal yield of the sensor can be increased.

According to a proposal of the invention the excitation radiation can be fed into the sensor most effectively if the end of a lightguide, in particular a single optical fiber, ends in the zones transparent to the excitation radiation, and if a filter layer is provided, in particular an optical interference filter, in the zones transparent to the excitation radiaton. In this manner the optimum wavelength for excitation of the indicator can be filtered out of the excitation radiation directly in the sensor. The electric wires carrying the measuring signals preferably are combined with the fiber, and standard plug-and-socket connections (for example of the BNC type, or similar connectors for connection of the lightguide) may be used for signal and light circuit.

In a preferred variant of the invention the photosensitive elements provided in microzones, as well as light-emitting sources placed in adjoining microzones, including their electric contact leads, are integrated on the carrier layer in planar arrangement, and the indicator substance of the indicator layer is in optical contact with the light-emitting sources and the photosensitive elements. The additional integration of the light-emitting sources will permit further miniaturization of the entire sensor unit. This sensor element only has electric connections, and all optical devices outside of the sensor element can be eliminated. In this variant a number of light-emitting or electroluminescent semiconductor zones are provided in adjacent microzones situated on a suitable carrier layer in a given topographical arrangement, with photosensitive semiconductor zones, e.g., photodiodes, phototransistors, being interposed in close proximity. Such light-emitting sources can be configured as light-emitting diode structures or as thin-film structures (cf. H. Antson et al: Characterization of Thin-Film Electroluminescent Structures by SIMS and Other Analytical Techniques; Anal. Chem, (1985) 322, p 175–180) with electroluminescent properties. Such semiconductor structures can be deposited on a suitable substrate to a thickness of a few $\mu$m by means of standard microelectronic techniques. The light-emitting zones or sources are electrically connected in such a way that they are stimulated jointly to emit the desired light radiation upon application of a given voltage or a flow of current of a given intensity. Semiconductor technology specifies a number of materials from which light-emitting diodes or electroluminescent layers must be made in order to emit a certain desired wavelength upon electric excitation. Another advantage of this sensor is that it is well suited for mass-production.

For determining electrolyte concentrations in aqueous solutions the difference in potential arising at the ion-selective layer of an ion-selective electrode, which is used as a measure for the electrolyte concentration, can be measured according to a prior proposal by providing the ion-selective layer with a potential-sensitive fluorescent indicator whose intensity of fluorescence is measured. If a sensor element as described by the invention is provided with an indicator layer according to the above proposal, a sensor of extremely small dimensions is obtained.

For distribution of the emitted and reflected light it may again be necessary according to the invention to provide an optically transparent coupling layer between the light-emitting sources and/or the photosensitive elements on the one hand and the indicator layer on the other hand.

As it may not be possible to integrate the light-emitting sources and the photosensitive elements on the same substrate, the proposal is put forward in a further development of the invention that the semiconductor structures constituting the light-emitting sources and, possibly, their electric contacts, be integrated on a separate substrate which is deposited in those microzones of the carrier layer carrying light-emitting sources. For example, a base substrate, i.e., the carrier layer, suitable for carrying the one kind of photo-semiconductors (e.g., the photosensitive elements), is coated with a co-substrate in those places where the other structure is to be integrated subsequently. It will also be possible, of course, to provide an additional co-substrate prior to adding the photosensitive elements.

In principle, there are no limitations with regard to the topographic arrangement of the light-emitting and light-sensitive elements. It is essential, however, that one or more light-emitting sources should be placed next to one or more photosensitive elements. For example, the invention permits a chessboard-type pattern of the microzones on the carrier layer, in which these wavezones are provided alternately with a light-emitting source and a photosensitive element.

Another variant of the invention proposes that the microzones be arranged on the carrier layer in honeycomb fashion, i.e., each light-emitting source is surrounded by two or more equidistant photosensitive elements coated with different filter materials. Due to its geometric emission characteristic, each light-emitting source will reach only a certain part of the indicator substance in the superimposed indicator layer, which it will stimulate to give off fluorescent light. The fluorescent light of the indicator substance will then be emitted uniformly in all directions and will reach at least two of the equidistant photosensitive elements. These elements are coated with filter materials of different transparencies for different wavelengths, and are able to determine the intensity of the fluorescence spectrum in several wavelength ranges at the same time. Using the above hexagonal honeycomb structure it will also be possible to surround the photosensitive elements with several light-emitting sources each, if the signal yield of the sensor element can be increased in this way.

Finally, yet another arrangement provides that the light-emitting sources, preferably LEDs, each be surrounded by a photosensitive element of an annular structure, preferably a photodiode or a phototransistor. In this variant transmitter and receiver, e.g., photodiode and phototransitor, will form an integral unit. The advantage of this arrangement is its better utilization of the reflection or fluorescence of the indicator molecules, as there will be a much greater overlap between angle of a mission of the light source and angle of acceptance of the photoreceiver. Instead of the annular structures, quadrangular structures may be used. Once again, several such arrangements can be connected in parallel and can be sensitized to respond to various analytic quantities by coating them with the appropriate indicator layers or optical filters.

The arrangements described so far are preferably designed for use with fluorescent indicator dyes, although absorption indicators may be used as well. Fluorescent indicators have the advantage that the wavelength of the excitation light is clearly separated from that of the fluorescent light by the so-called Stokes shift, i.e., a difference in wavelength, and that the two wavelengths can be separated sharply by optical filters at the light-emitting sources or at the photosensitive elements, or at both sites, which will be an additional means of avoiding interferences during measurement.

The problem that it may not be possible to provide the light-emitting sources and the photosensitive elements on the same carrier layer and that there may be no suitable co-substrate, is avoided in another variant of the invention, in which the light-emitting sources on the one hand and the photosensitive elements on the other hand are provided in planes parallel to each other, the light-emitting sources preferably forming a continuous luminescent layer covering the carrier layer, and in which the semiconductor structures constituting the photosensitive elements are integrated on a substrate covering the luminescent layer, and in which this substrate is provided with zones permitting optical contact between the luminescent layer and the indicator layer. The photosensitive elements may be placed on a base substrate and may be covered by the layers described before, including the indicator layer. Underneath this substrate featuring optically transparent zones there are situated the light-emitting sources of a suitable wavelength which will give off excitation light via the open spaces between the photosensitive elements. The light sources may also be configured as a single electroluminescent layer, for example. In another possible variant the sensor structure, which does not contain any light-emitting elements as such, could be applied on a separately produced light-emitting element with the use of a hybrid technique, e.g., bonding.

In non-transparent substrates the zones of the substrate required for optical contact can be obtained by etching out holes or by cutting out perforations with the use of laser techniques.

It is obvious that the above-described principle of placing the electro-optical elements in different planes may also be practised in reverse, such that the light-emitting sources are provided on a transparent substrate and that the photosensitive elements are situated underneath this substrate.

In an enhanced version of the invention an optical filter layer is provided between the luminescent layer and the substrate carrying the photosensitive elements.

A further development of the invention provides that the coupling layer should contain a diffraction structure, for instance, a periodic lattice structure directing the excitation radiation into the areas of the indicator layer situated above the photosensitive elements. The diffraction structure in the coupling layer is used as a focusing optical element for the excitation radiation, the small height of such structures (holographic structures) being of advantage. In order to utilize the holographic structures, which can be made to a thickness of 0.3 $\mu$m, most effectively, parallel light of a small spectral bandwidth is recommended, although such structures will be effective even in case of divergancies of some 5 to 10 degrees and a spectral bandwidth of some 5 to 10 nm.

For better separation of the excitation light from the fluorescent light and for evaluation with regard to several different wavelengths, it is proposed in a further development of the invention that the photosensitive elements and/or the light-emitting sources be additionally coated with an optical filter layer, preferably an optical interference filter. If a suitable fluorescent indicator is chosen or if diffuse reflection is being measured, it may not be necessary for each of the two photoelectric elements to be coated with a filter layer.

In a further development of the invention the dependence of the spectral transparency range of interference filters on angles of light incidence is made use of, with an interference filter situated between the coupling layer and the indicator layer, which has different transmission coefficients for the excitation radiation and the fluorescent radiation emitted by the indicator, depending on given angles of incidence. It is known that with interference filters the range of transparency will shift towards the shorter wavelengths if the incident radiation does not arrive at a right angle to the surface of the filter. Thus the angle-dependent spectral shift of the transparency range of interference filters can be used for differentiating between excitation light of a short wavelength and fluorescent light of a longer wavelength. Short-wave excitation light can penetrate the filter layer only if the angle of incidence $\alpha$ is greater than a given limiting angle, say 30°. Longer-wave fluorescent light will penetrate the filter layer only if the angle of incidence $\beta$ is smaller than a given limiting angle, say 25°. Due to these optical circumstances the position of the photosensitive elements or the light-emitting sources relative to the indicator layer can be optimized to obtain the maximum signal yield. If light of a longer wavelength (whose spectrum corresponds to that of the fluorescent light) is emitted by the light-emitting sources, e.g., LEDs, corresponding angle conditions should apply, which will prevent longer-wave light emitted by the LEDs, or the respective scattered light, from reaching the photosensitive element, e.g., the phototransistor.

If several substance concentrations are to be determined in gaseous or liquid samples at the same time, a variant of the invention specifies that the indicator layer is provided with microzones corresponding to individual photosensitive elements and containing different indicators. In this way one sensor element, in which the topographic arrangement of light-emitting and photosensitive elements may be freely chosen, can be employed for measuring several different substances from the same sample simultaneously.

In this context a preferred development of the invention proposes that the indicator layers should be made of porous glass containing the indicator in immobilized form.

For manufacture of a pH-sensor, microporous glass is used for instance, which is deposited by sputtering. The indicator dye is chemically immobilized on this layer, upon which a protein-impermeable layer, for example consisting of crosslinked polyvinyl alcohol, may then be vapor-deposited. According to another proposal of the invention, the indicator layer could be a silicon film that may be applied by spinning or rolling, in which the indicator is contained.

A special variant of the invention provides that the indicator molecules of the indicator substance be chemically bonded to the optical coupling layer. If the material used for the optical coupling layer is not suitable for direct immobilization, it may be provided with a coating of some other material, e.g., a suitable kind of glass, which will lend itself to the chemical immobilization of indicator molecules.

In order to permit the application of different indicator substances in areas of the indicator layer of a few 100 $\mu$m diameter only, techniques such as micro-screenprinting or evaporation coating can be used. For this purpose thin layers of material are deposited by micro-screenprinting or similar techniques on certain zones which are defined by a mask, which in turn is produced by a photographic process.

The indicator layer could also be provided with a cover layer on the side next to the sample. In the simplest variant this cover layer may consist of a pigmented polymer film which will prevent the excitation light and the fluorescent light from entering the sample chamber where they might stimulate undesirable reflections or fluorescences that would enter into the measurement as interferences. The use of such a cover layer would also make irrelevant any differences in the refractive indices of different sample materials. Besides, a suitable cover layer will help protect the indicator layer from macromolecular components of the sample, which would influence the measured result. It is also possible to provide a cover layer with selective properties such that the substances to be measured are enabled to diffuse into the indicator layer before all others. For those variants in which the coupling layer has the function of a lightguide, a cover layer with a suitable refractive index may be selected, such that the cover layer will assume the task of the boundary layer next to the sample. With sensor elements which do not utilize fluorescence, but absorption or diffuse reflection of the indicator, it is usually necessary to provide the boundary layer between indicator and sample with a reflective coating, with the possible addition of an optical cover layer.

In addition to the possibilities of mass-production opened up by microelectronic techniques, another advantage of such planar microsensors is that electronic circuits are integrated on the carrier layer and any other substrates bonded thereto, which are designed for controlling the brightness of the radiation generated by the light-emitting sources and/or for amplifying the electric signals of the photosensitive elements. According to the invention, even further integration is achieved by providing the carrier layer with highly integrated electronic circuits for signal evaluation tasks. For example, if differently pigmented layers of glass are deposited on the light-sensitive elements of individual microzones by sputtering, and if this color pattern, or rather the filters with their different transparency ranges, are taken into account in the microelectronic circuit, i.e., by assigning circuit I to color I and circuit II to color II, etc., multi-wavelength analysis will be possible directly in the sensor element.

It is also possible to cover part of the photosensitive elements with the same filter materials as the light-emitting sources. In this instance scattered or reflected excitation light is detected, which will provide a reference value for light intensity.

DESCRIPTION OF THE DRAWINGS

The invention will now be further illustrated with reference to the accompanying drawings, in which FIG. 6 shows the sensor element according to FIG. 5 cut parallel to its surface, along line VI-VI in FIG. 5, FIGS. 7-9 present other variants of the sensor element, in the same sectional view as FIG. 5, and FIGS. 10a, 10b and 11 present sensor elements with different topographical arrangements of the photoelectric elements, FIG. 10b being an end view of FIG. 10a.

DETAILED DESCRIPTION OF THE PREFERRED EMBODIMENTS

Figure 1:
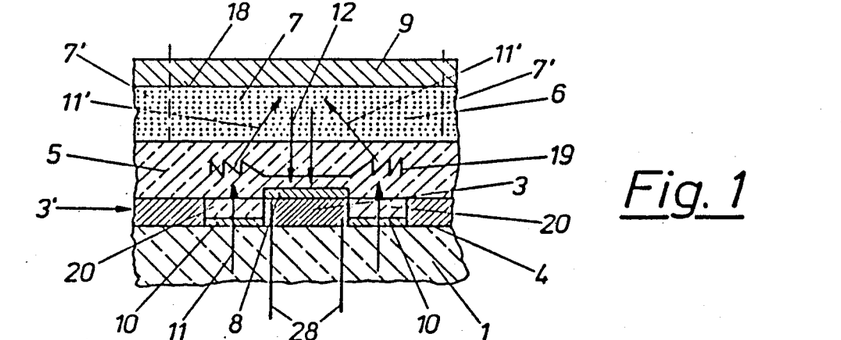
FIG. 1 is a schematic view of a section through a sensor element as described by the invention.
Figure 4:
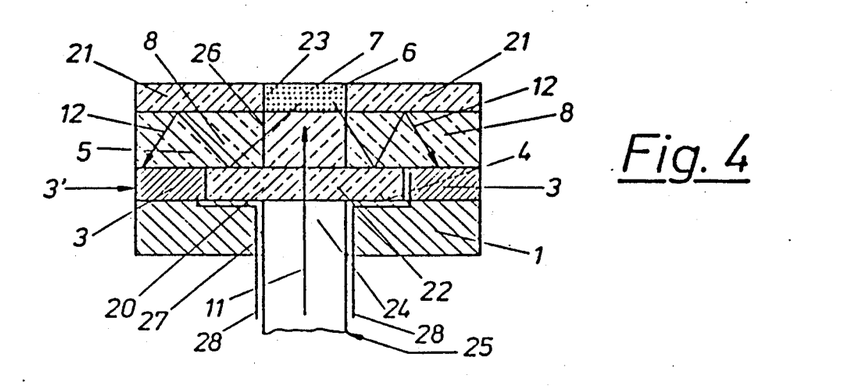

FIG. 1 shows a sensor element as described by the invention, comprising photosensitive elements 3 in a thin-film substrate 3' on a suitable carrier layer 1, which elements are integrated into this substrate in planar arrangement, parallel to the surface 4 of the carrier layer 1. The photosensitive elements 3 are covered by an optically transparent coupling layer 5, for instance made of $SiO_2$, which is deposited by suitable microelectronic techniques. It is also possible, however, to place the photosensitive elements 3 directly on the carrier layer 1; in this case the coupling layer 5 will also cover the spaces between the photosensitive elements 3. On top of this coupling layer 5 is the indicator layer 6 containing the indicator substance 7. The substrate 3' features zones 20 which are transparent to the excitation radiation 11, the latter being introduced via the transparent carrier layer 1—for instance by means of optical fibers not shown here. In order to obtain the wavelength desired for excitation of the indicator substance 7 the transparent zones 20 are provided with a filter layer 10. After passage through this filter layer the excitation radiation 11 will arrive at a diffraction structure 19 contained in the coupling layer 5, for example a holographic lattice structure or blaze, such that the excitation radiation 11' deflected by this structure is directed into the areas of the indicator layer 6 situated above the photosensitive elements 3. The electric contacts of the photosensitive elements 3 covered by an optical filter material 8 are not shown in detail in the individual figures, as they are integrated in the carrier layer 1, or rather in the substrate 3', by means of standard microelectronic techniques; only the contact pins and wires 28 leaving the sensor element through the carrier layer 1 are shown in FIG. 1 and FIG. 4 to be discussed below; according to the invention these pins and wires could also be located in other places of the sensor element. In order to prevent excitation radiation 11 from leaving the sensor element, which might lead to undesirable reflections or fluorescences in the adjoining sample, the indicator layer is provided with an optical cover layer 9 on its side 18 next to the sample, such that only fluorescent radiation 12 or reflected radiation from the sensor layer 6 is detected. It will also be possible, of course, to provide different indicator substances 7, 7' in individual areas of the sensor layer 6 corresponding to specific photosensitive elements 3.

In all other embodiments of the invention identical parts have identical reference numbers.

Figure 2:
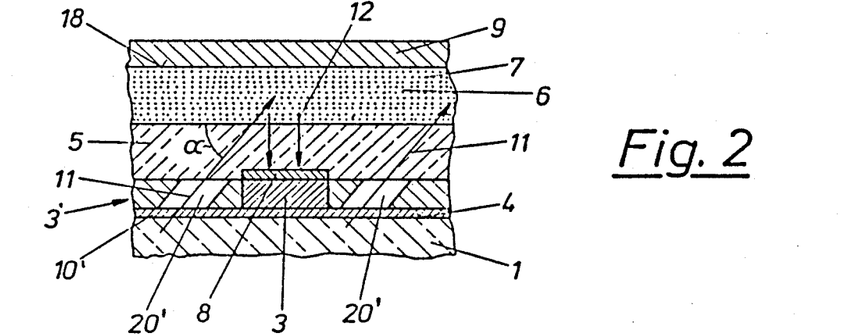
FIG. 2 shows a variant of the sensor element of FIG. 1, in the same sectional view.

In the variant shown in FIG. 2, another approach is used to realize the most advantageous conditions of excitation and detection. The excitation radiation 11 introduced through the transparent carrier layer 1 is directly transmitted into the areas of the indicator layer 6 located above the photosensitive elements 3 via transparent zones 20° in the substrate 3' that are positioned at an angle. The angle between excitation radiation 11 and indicator layer 6 is defined by the topographical arrangement of the photosensitive elements and the transparent zones as well as by the thickness of the individual layers, especially the coupling layer 5. It can be between 40 and 60. In the example presented in FIG. 2 it is approximately 45°. Between the carrier layer 1 and the substrate 3' is provided an optical filter layer 10' for filtering out the best wavelength of excitation of the indicator substance 7. The slanting openings or transparent zones 20' in the substrate 3' can be produced by techniques such as laser perforation.

Figure 3:
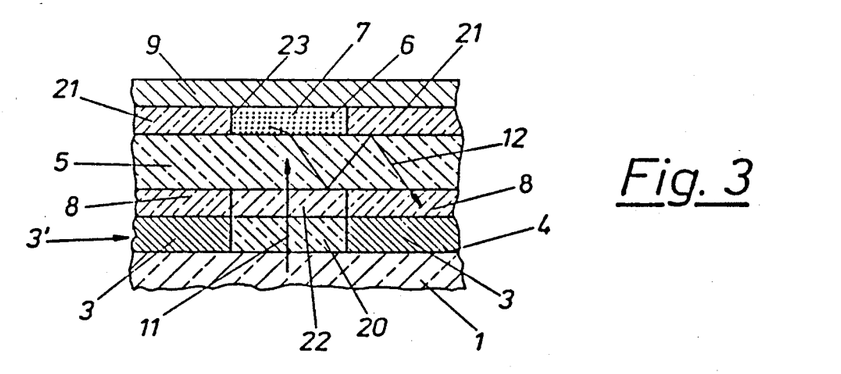
FIGS. 3 and 4 present other variants of the sensor element, again in the same sectional view as FIG. 1.

FIG. 3 presents a sensor element with a transparent carrier layer 1 coated by a substrate 3' configured as a diode layer. This diode layer is provided with transparent zones 20 which are etched out for passage of the excitation radiation on its way to the indicator layer 6 containing the indicator substance 7 on top of the transparent zones. The coupling layer 5 on top of the diode layer, with a refractive index $n_2$, is bounded on either side by boundary layers 21, 22 with a refractive index $n_1$, such that the coupling layer 5, together with the boundary layers 21, 22, will form a planar lightguide for the radiation 12 to be measured In the boundary layer 21 facing the sample recesses 23 are made by etching, in which the sensor layer 6 is deposited. The cover layer 22 applied on the side facing away from the sample is replaced by a filter layer B in the area of the photosensitive elements 3 (photodiodes), with a refractive index $n_3$ at which there is no total reflection of the excitation radiation ($n_3$ approx. equal to $n_2$). The excitation radiation 11 arriving normal to the boundary layer 22 will pass the coupling layer 5 and enter the sensor layer 6 where it will excite the indicator substance 7. The fluorescent radiation 12 emitted in all directions is partly subject to total reflection at the boundary layers 21, 22 and will enter the photosensitive elements 3 in the areas of the filters 8 where no total reflection occurs. Of course, this sensor may also be shielded against the sample by means of a cover layer 9.

The sensor element shown in FIG. 4 is a variant of that in FIG. 3. In this case a wafer (carrier layer 1 plus substrate 3') is used as a starting material, which incorporates all the layers of a photodiode, marked 3' in this Figure. From this wafer an annular photosensitive element 3 is etched out, and the circular center area is filled up homogeneously with glass (refractive index $n_1$), for instance by sputtering, thus producing zone 20 which is transparent to the excitation radiation 11. This is then coated with a coupling layer 5 made of a colored glass filter material deposited by sputtering, or of a plastic filter material applied by spinning, with a refractive index $n_2$. In this case the coupling layer 5 acts both as a lightguide for the radiation to be measured 12 and as a selective filter layer B which separates the fluorescent radiation from the reflected or scattered radiation. From the filter layer B an opening 26 is etched out, which is situated above the transparent zone 20 and which is then filled with glass that is transparent to the excitation radiation 11. Finally, the boundary layer 21 next to the sample, which has a refractive index $n_1$, is applied by sputtering or spinning, and the indicator layer 6 is deposited in the recess 23 concentric with the opening 26. The indicator layer 6 either consists of porous glass containing the indicator 7 in immobilized form, or of a silicone material containing the indicator, which is pressed into the disk-shaped recess 23 by a roller. It will be of advantage if the refractive index of the indicator layer 6 is similar to that of the coupling layer 5.

As a final step the carrier layer 1 is provided with a center bore 27 extending as far down as the boundary layer 22 filling the transparent zone 20 and containing the end 24 of a lightguide 25, preferably a single optical fiber. The contact wires 28 leave the structure parallel to the lightguide 25, and may form an optoelectric fiber bundle if suitably attached to the lightguide.

Figure 5:
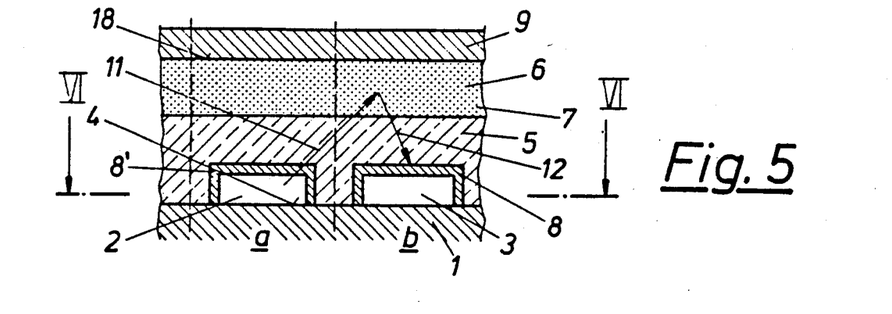
FIG. 5 is a section along line IV-VI in FIG. 6 through another variant of a sensor element.
Figure 6:
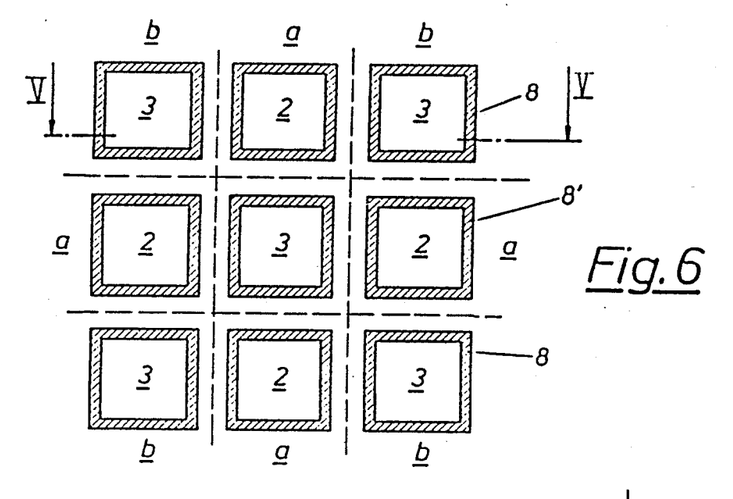

The sensor element in FIG. 5 has a carrier layer 1 which is divided into microzones a, b in chessboard fashion, alternately featuring light-emitting sources 2 in microzones a and photosensitive elements 3 in microzones b, which sources or elements are integrated in planar arrangement parallel to the surface 4 of the carrier layer 1. The topographical arrangement of the microzones a, b described by this example is shown in FIG. 6; the sides of the individual microzones are only a few $\mu$m long. The photoelectric elements 2, 3 are covered by an optically transparent coupling layer 5, e.g., of $SiO_2$. In order to obtain the wavelength desired for excitation of the indicator substance 7, the light-emitting sources 2 configured as LEDs or electroluminescent layers may be coated by an optical filter material 8'; it will also be possible to coat the photosensitive elements 3, e.g., phototransistors, with an optical filter material 8 in order to select a given wavelength from the fluorescence spectrum. The electric leads into the light-emitting sources 2 and the signal leads from the photosensitive elements 3 are not shown here.

Figure 7:
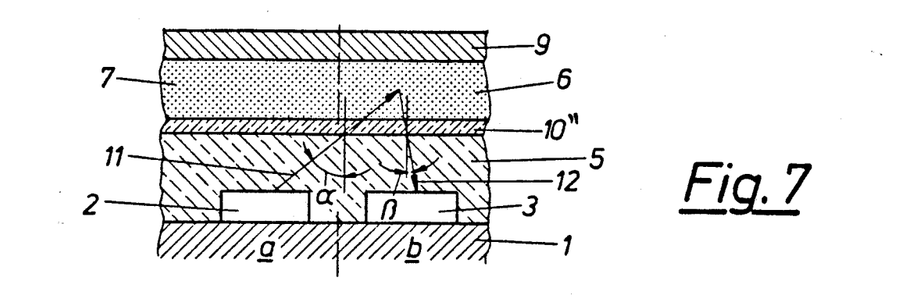

The variant presented in FIG. 7 shows that the angle-dependent spectral shift of the transparancy range of an interference filter 10" between the coupling layer 5 and the indicator layer 6 may be used for differentiating between short-wave excitation radiation 11 and longer-wave fluorescent radiation 12. As in FIG. 5, the light-emitting sources 2 and the photosensitive elements 3 are arranged in one plane. The geometrical arrangement of the photoelectric elements 2, 3 relative to each other and to the interference filter 10 and the indicator layer 6 on top of it will result in the following: Short-wave excitation radiation 11 can only pass the interference filter 10" if the angle of incidence $\alpha$, measured against the normal on the interference filter, is greater than a given limiting angle, say 30°. Longer-wave fluorescent radiation 12 will pass the interference filter 10" only if the angle of incidence $\beta$ is smaller than a given limiting angle, say 25°. This advantageous positioning of an interference filter may also be used if the light-emitting sources and the photosensitive elements are not situated in the same plane.

Figure 8:
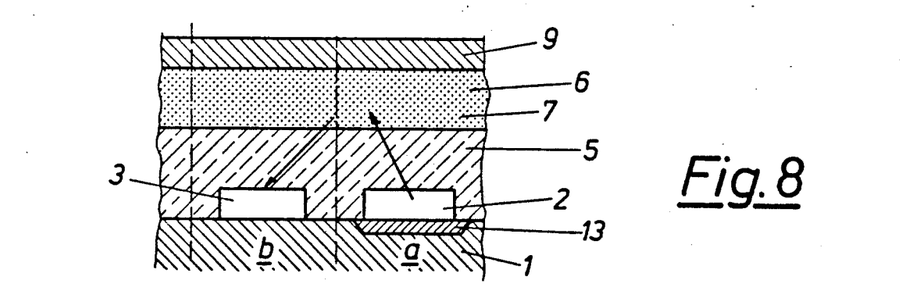

If the light-emitting sources 2 and the photosensitive elements 3 cannot be integrated on the same carrier layer 1, it is possible—as shown in FIG. 8—to provide specific microzones b of the carrier layer 1 with one kind of photoelectric elements, for instance the photosensitive elements 3, while those microzones a of the carrier layer 1 designed for containing the light-emitting sources, are coated with another substrate 13 (co-substrate prior to integration of these elements. It is furthermore possible to use a separate co-substrate for the photosensitive elements 3, or different substrates for each kind of photoelectric elements 2, 3.

Figure 9:
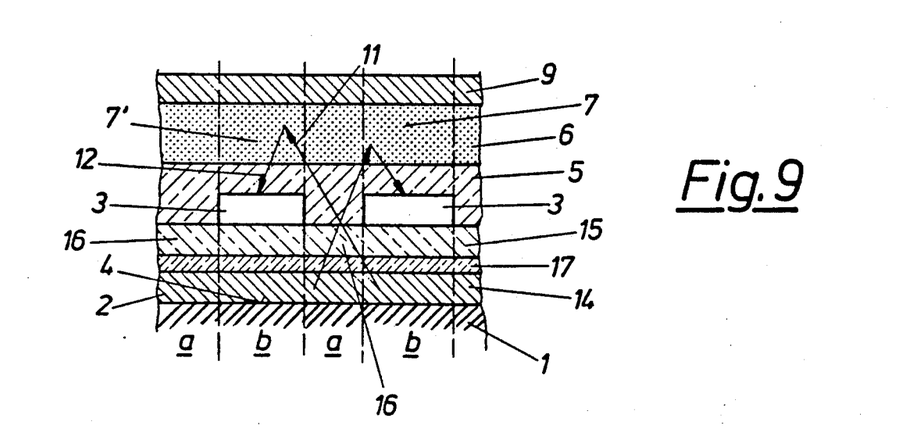
Figure 10A:
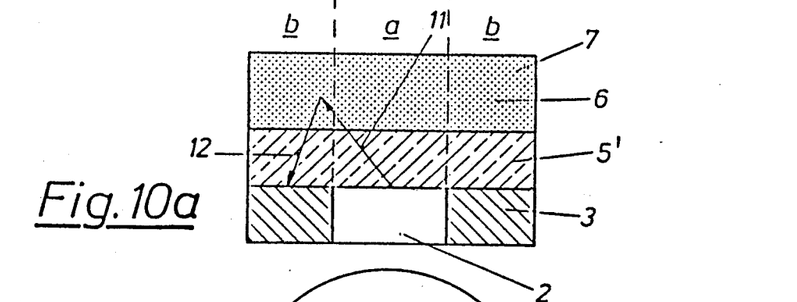
Figure 10B:
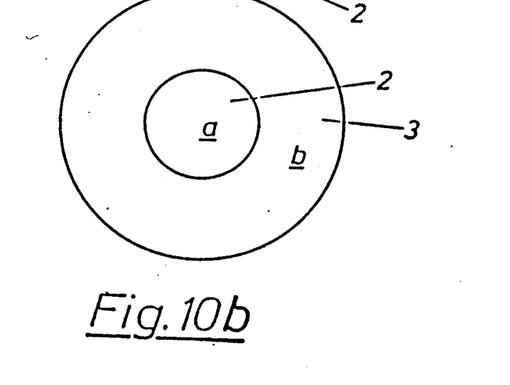

In the variant presented in FIG. 9 the light-emitting sources 2 and the photosensitive elements 3 are not arranged in one plane. The light-emitting sources 2 integrated on the carrier layer 1 in microzones a may form a continuous, luminescent layer 14, as is shown here; in this instance the microzones a, b will overlap at least in parts. The luminescent layer 14, which may be coated by a filter layer 17, is then covered by a substrate 15 on which the photosensitive elements 3 are integrated in microzones b. On top of this substrate are deposited the coupling layer 5 and the indicator layer 6 which may be provided with a cover layer 9. The substrate 15 carrying the photosensitive elements 3 either is transparent to the excitation radiation 11 altogether, or at least has zones 16 where this transparency may be obtained by etching out holes or cutting out perforations with the use of a laser technique. As in the sensor shown in FIG. 5, the photosensitive elements and the light-emitting sources of this variant also may be coated with different filter materials, or individual photosensitive elements 3 may be coated with different filter materials each, in order to permit evaluation of the fluorescent radiation 12 for several different wavelengths. Individual microzones b of the sensor layer 6, which correspond to the photosensitive elements 3, also may be provided with different indicator substances 7,7', which will ensure that the concentrations of several substances contained in the sample can be determined simultaneously with the use of one sensor element. In the configuration presented in FIGS. 10a and 10b the light-emitting source 2 and the photosensitive element 3 form an integral unit of an annular structure. In this variant a photodiode in the circular microzone a may be surrounded by a phototransistor in the circular microzone b, for instance. Several such integral units may be combined into a sensor element.

Figure 11:
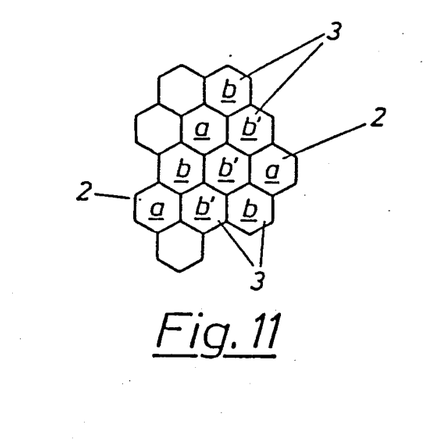

FIG. 11 finally presents yet another topographical arrangement of the microzones, featuring a hexagonal honeycomb structure. In this example a light-emitting source is surrounded by several photosensitive elements 3 all placed at the same distance from the source. This advantageous arrangement will permit the performance of multi-wavelength analysis in a simple manner, i.e., by using different filter materials in the microzones b, b'.

We claim:

1. An electro-optical sensor element for determining the concentration of substances contained in gaseous and liquid samples, comprising
    a carrier layer,
    a thin-film substrate comprising at least one photosensitive element, a plurality of electrical contacts and at least one area which is transparent to excitation radiation associated with said carrier layer by microelectronic and photolithographic techniques,
    an indicator layer, and
    a transparent coupling layer located between said thin-film substrate and said indicator layer, said transparent coupling layer containing a diffraction structure,
    said indicator layer being produced by microelectronic and photolithographic techniques and comprising at least one indicator substance having optical properties, at least one of the optical properties of said indicator substance changing upon interaction with said substances contained in said gaseous and liquid samples depending on the concentrations of said substances in said gaseous and liquid samples, and wherein said indicator substance of said indicator layer, which is excited by a source of excitation radiation, is in optical contact with said at least one photosensitive element via said transparent coupling layer, said diffraction structure directing said excitation radiation into areas of said indicator layer facing said at least one photosensitive element.

2. An electro-optical sensor element according to claim 1, wherein said diffraction structure is a periodic lattice structure.

3. An electro-optical sensor element for determining the concentration of substances contained in gaseous and liquid samples, comprising
    a carrier layer, a thin film substrate comprising at least one photosensitive element, a plurality of electrical contacts and at least one area which is transparent to excitation radiation associated with said carrier layer by microelectronic and photolithographic techniques,
an indicator layer,
a transparent coupling layer located between said thin-film substrate and said indicator layer,
said indicator layer being produced by microelectronic and photolithographic techniques and comprising at least one indicator substance having optical properties, wherein at least one of the optical properties of said indicator substance will change upon interaction with said substances contained in said gaseous and liquid samples depending on the concentrations of said substances in said gaseous and liquid samples, and wherein said indicator substance of said indicator layer, which is excited by a source of excitation radiation, is in optical contact with said at least one photosensitive element via said transparent coupling layer, and
transparent areas positioned in said thin-film substrate at an angle, such that said excitation radiation will strike said indicator layer at an angle a of 40° to 60°, exciting areas of said indicator layer facing said photosensitive elements.

4. An electro-optical sensor element for determining the concentration of substances contained in gaseous and liquid samples, comprising
a carrier layer,
a thin film substrate comprising at least one photosensitive element, a plurality of electrical contacts and at least one area which is transparent to excitation radiation associated with said carrier layer by microelectronic and photolithographic techniques,
an indicator layer,
a transparent coupling layer located between said thin-film substrate and said indicator layer,
said indicator layer being produced by microelectronic and photolithographic techniques and comprising at least one indicator substance having optical properties, wherein at least one of the optical properties of said indicator substance will change upon interaction with said substances contained in said gaseous and liquid samples depending on the concentrations of said substances in said gaseous and liquid samples, and wherein said indicator substance of said indicator layer, which is excited by a source of excitation radiation, is in optical contact with said at least one photosensitive element via said transparent coupling layer, and wherein said coupling layer, which has a refractive index $n_2$, together with boundary layers situated on both sides of said coupling layer, which have a refractive index $n_1$, constitute a planar lightguide for said radiation to be measured, with $n_2 > n_1$, wherein said boundary layer adjacent to said sample has at least one recess which is covered by said indicator layer, and wherein each of said recesses, seen in a direction of said excitation radiation, is situated above one of said areas transparent to said excitation radiation, and wherein total reflection of said radiation to be measured is cancelled in areas of said photosensitive elements.

5. An electro-optical sensor element according to claim 4, with only one of said areas transparent to said excitation radiation and wherein said photosensitive element has an annular structure concentric to said area.

6. An electro-optical sensor element according to claim 1, 3 or 4, wherein one end of a lightguide extends to said areas transparent to said excitation radiation.

7. An electro-optical sensor element according to claim 1, 3 or 4, wherein said areas transparent to said excitation radiation are provided with a filter layer.

8. An electro-optical sensor element according to claim 7, wherein said filter layer is an optical interference filter.

9. An electro-optical sensor element according to claim 1, 3 or 4, wherein said photosensitive elements are additionally coated with an optical filter layer.

10. An electro-optical sensor element according to claim 1, 3 or 4, wherein an interference filter is situated between said coupling layer and said indicator layer, which has different transmission coefficients for said excitation radiation and said fluorescent radiation emitted by said indicator substance.

11. An electro-optical sensor element according to claim 1, 3 or 4, wherein said indicator layer is provided with microareas corresponding to individual photosensitive elements and containing different indicators.

12. An electro-optical sensor element according to claim 1, 3 or 4, wherein said indicator layer is made of porous glass containing said indicator in an immobilized form.

13. An electro-optical sensor element according to claim 1, 3 or 4, wherein said indicator layer is a silicone film which is applied by spinning or rolling, and in which said indicator is contained.

14. An electro-optical sensor element according to claim 1, 3 or 4, wherein indicator molecules of said indicator substance are chemically bonded to said transparent coupling layer.

15. An electro-optical sensor element according to claim 1, 3 or 4, wherein said indicator substances are deposited by techniques such as micro-screenprinting or evaporation coating.

16. An electro-optical sensor element according to claim 1, 3 or 4, wherein electronic circuits are integrated on said carrier layer, said circuits being designed for amplifying electric signals produced by said photosensitive elements.

17. An electro-optical sensor element according to claim 16, wherein said carrier layer is provided with highly integrated electronic circuits for signal evaluation tasks.

18. An electro-optical sensor element according to claim 1, 3 or 4, wherein said microelectronic and photolithographic techniques comprise evaporation coating, sputtering, spinning, etching and ion beam erosion.

* * * * *